United States Patent [19]

Weigle et al.

[11] Patent Number: 4,502,475
[45] Date of Patent: Mar. 5, 1985

[54] DRILL GUIDE FOR BONE PLATE FIXATION

[75] Inventors: Robert M. Weigle, Adelphi; Sharon Duggan, Owings; Candace Foster, Clarksville; Jonathan Miner, Bowie; John Vantucci, Catonsville; Mark Woozley, Frederick, all of Md.

[73] Assignee: The United States of America as represented by the Department of Health and Human Services, Washington, D.C.

[21] Appl. No.: 468,776

[22] Filed: Feb. 22, 1983

[51] Int. Cl.$^3$ .................................................. P61F 5/04
[52] U.S. Cl. ............................... 128/92 EB; 128/92 R
[58] Field of Search .............. 128/92 R, 92 E, 92 EB, 128/303 R

[56] References Cited

U.S. PATENT DOCUMENTS

| | | | |
|---|---|---|---|
| 3,835,849 | 9/1974 | McGuire | 128/92 EB |
| 4,119,092 | 10/1978 | Gil | 128/92 EB |
| 4,360,012 | 11/1982 | McHarrie et al. | 128/92 EB |
| 4,364,381 | 12/1982 | Sher et al. | 128/92 EB |

OTHER PUBLICATIONS

J. R. Siebrandt Mfg. Co. Catalog, pub. 7/1/39, "Goodwin Bone Clamp & Drill Guide".

Zimmer, "No. 271 Key Guide for Dual Plates", p. 32, 2/1/47.

Primary Examiner—C. Fred Rosenbaum
Assistant Examiner—C. W. Shedd
Attorney, Agent, or Firm—Browdy and Neimark

[57] ABSTRACT

A drill guide device for bone plate fixation, consisting of an elongated drill guide block having a longitudinal recess for receiving and positioning a bone plate having screw openings. The guide block has spaced openings axially aligned with the bone plate screw openings and containing removable drill guide bushings. The guide block is longitudinally slotted at its ends for adjustable attachment to clamp blocks carrying respective bone-engaging scissor clamp assemblies connected by tie rods. The tie rods have oppositely threaded ends which are threadedly engaged with the respective clamp blocks. The tie rods have hexagonal center portions shaped for driving engagement by a wrench. The scissor clamp assemblies have upstanding opposite top handle portions connected by clamping screws, each clamping screw being pivotally connected to one handle portion and extending through the opposite handle portion. The outer end portion of each clamping screw is provided with a clamping nut. The clamp assemblies have opposing bone-engaging jaw elements moved towards each other when the associated clamping nuts are tightened. Delrin pad elements are provided on the bone-contacting surfaces.

16 Claims, 7 Drawing Figures

DRILL GUIDE FOR BONE PLATE FIXATION

FIELD OF THE INVENTION

This invention relates to drill guide devices, and more particularly to a drill apparatus to provide improved alignment of pilot drill holes for screw attachment of bone plate fracture fixation devices.

BACKGROUND OF THE INVENTION

The present art of drilling pilot holes for fixating a bone plate relies totally on the surgeon's skill to accurately align and space screw pilot holes using a pneumatic power drill. The procedure is often complicated by the presence of body tissue, blood, and other body fluids in the operating field.

A bone plate is a device used in orthopedic surgery to secure and stabilize a very severe fracture. The plate is screwed into place over the fracture and the broken bones are thereby held together. A portion of the load applied to the bone is supported by the plate during the healing process. An example of one type of bone plate is shown in FIG. 2. Several screws are used to secure the plate to the bone segments. Different styles and lengths of these plates are used, depending on the type and location of the fracture.

The kind of fracture fixation involving the use of a bone plate is called "open reduction" and requires a surgical incision. Bone plates are used for very severe fractures, when fast healing is needed, or for very traumatized fractures where tissure damage already exists and there is no additional risk in surgery. Bone plates would probably not be used on the more simple transverse and oblique fractures. A cast would then provide the necessary stabilization.

If a bone plate is to be used, screw pilot holes are drilled into the bone. A pneumatic drill is usually employed to make these pilot holes for the screws, usually relying on the surgeon's skill to accurately align and space the holes. The operating site is not ideal for accurately positioning bone screws. In most cases, the body tissues are not completely cleared from the bone and the area is covered with blood and other body fluids.

A major problem in fracture fixation is to obtain accurate alignment of the pilot holes normal to the surface of the bone. In many cases, a surgeon will have difficulty in aligning the holes, and consequently the bone plate will not be securely attached to the bone. Misaligned screws can cause stress concentrations in the plate and perhaps cause splintering of the bone. Uneven stress distributions in the screws can be created by poor spacing of the pilot holes. Fracturing of the plate and screws, as well as fretting corrosion are not uncommon. There is a need for a drill guide with a clamping mechanism that would aid the surgeon in aligning and spacing the pilot holes.

There are currently several types of drill guides available for surgical use. All of these guides are hand-held, and in most cases, each hole is drilled independently of the next. None of the prior art drill guides is fixed to the bone, thus allowing tilting and slipping during the drilling procedure. Quite often the bone plate is used as a drill guide. In such cases it is possible that during drilling the bone plate could be nicked or marred. Any damage to the bone plate increases the possibility of corrosion.

Corrosion is an important problem to be considered in any implant procedure. If an implant is not made of a biocompatible material, corrosion and subsequent tissue inflammation is the result. In the body environment the galvanic reaction between two dissimilar metals is enhanced. For example, problems could occur if a titanium alloy plate is secured with stainless steel screws. Evidence of corrosion has also been witnessed when the screwdriver and the screws are not of the same alloy. It is thought that metallic particles from the screwdriver blade are deposited in the head of the screw. Because of the complexity of the corrosion problem, all efforts should be made to protect the screws from contact with dissimilar metals. This problem must be taken into consideration in the design of a drill guide/clamping system.

A preliminary search of the prior art revealed the following prior U.S. Pat. Nos. of interest:
McElveny, 3,244,170;
McGuire, 3,835,849;
Gil, 4,119,092;
Cho, 4,257,411;
Sayegh, 4,349,017.

SUMMARY OF THE INVENTION

The drill guide and clamping mechanism of the present invention comprises a drill guide element which is clamped to the bone on both sides of the fracture. Holes for attaching the bone plate can then be accurately aligned and spaced, reducing the possibility of failure due to stress concentrations. The major components of the device are two clamps, two connecting rods, and a drill guide block with bushing inserts. Each clamp mechanism comprises a scissor arrangement with tripod jaws. The connecting rods hold the clamps a fixed distance apart. These rods also allow for adjustments of the bone plate position. The drill guide block, which contains the bone plate, attaches between the clamps. The bushing inserts, when placed in the block, guide the drill bit and are removed for insertion of the bone screws after the desired pilot holes have been drilled.

Accordingly, a main object of the invention is to provide an improved drill guide apparatus for obtaining improved alignment of pilot drill holes for screw attachment of bone plates to the segments adjacent to a fracture, the apparatus overcoming the deficiencies and disadvantages of the prior devices employed for forming the pilot holes.

A further object of the invention is to provide an improved drill guide and clamping system which will hold bone segments stable during an entire fracture fixation procedure and will ensure the correct placement and alignment of the screw pilot holes formed in the bone segments.

A still further object of the invention is to provide an improved bone drill guide and clamping sytem employing clamps of improved strength and durability.

A still further object of the invention is to provide an improved bone drill guide and clamping device whose use does not appreciably increase the wound size, does not cause lengthening of the operating procedure, and does not cause appreciable interference with retraction instruments.

A still further object of the invention is to provide an improved bone drill guide and clamping device which is easy to use, which is easy to sterilize, and which can withstand methods of sterlization without compromising mechanical integrity.

A still further object of the invention is to provide an improved bone drill guide and clamping apparatus which is adaptable for a wide range of bone diameters.

A still further object of the invention is to provide an improved bone drill guide and clamping apparatus which can be made of biocompatible materials to avoid problems associated with wear and corrosion.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
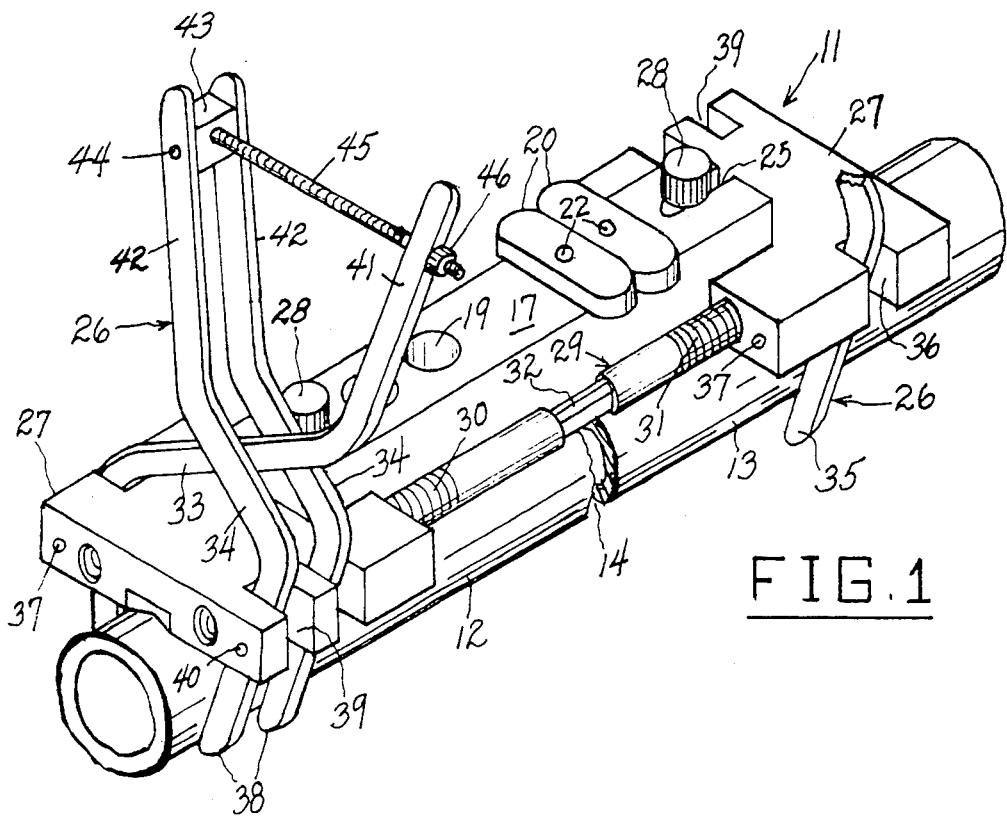
FIG. 1 is a perspective view of a typical bone drill guide and clamp device according to the present invention, shown operatively mounted over a fractured bone, the major portion of one of the scissor clamp members being broken away to reveal structural details of the assembly.
Figure 2:
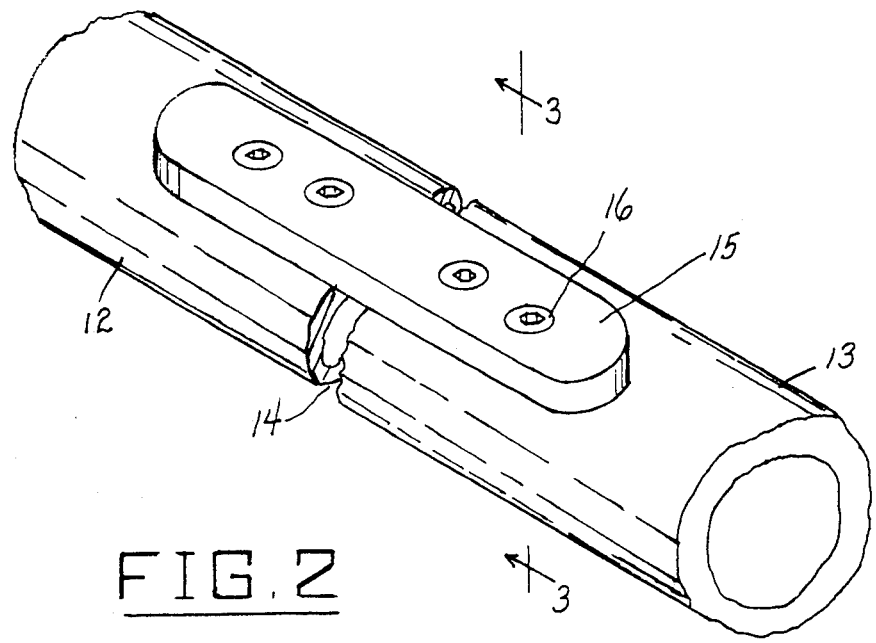
FIG. 2 is an enlarged perspective view of a typical bone plate secured to the bone segments on opposite sides of a fracture.
Figure 3:
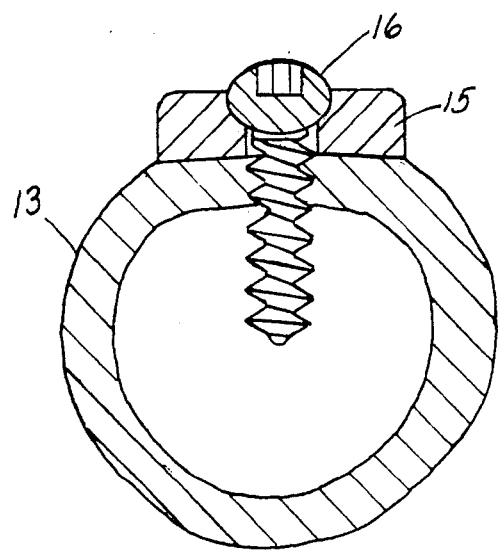
FIG. 3 is an enlarged transverse vertical cross-sectional view taken substantially on line 3—3 of FIG. 2.
Figure 5:
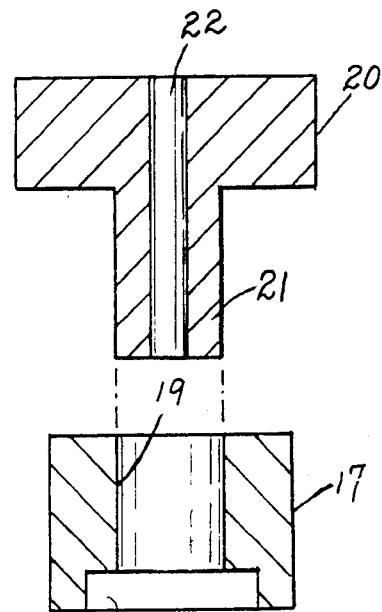
FIG. 5 is an enlarged transverse vertical cross-sectional view taken substantially on line 5—5 of FIG. 4.

Referring to the drawings, and more particularly to FIG. 1, 11 generally designates an improved drill guide apparatus according to the present invention, shown clampingly secured to bone segments 12 and 13 on opposite sides of a fracture 14, for holding a bone plate, similar to that shown at 15 in FIG. 2, on the bone segments 12 and 13 in a suitable position on the segments for drilling screw pilot holes for receiving Allen screws 16, employed to secure the bone plate to the segments in the manner illustrated in FIG. 3.

The bone plate 15 is a typical device used in orthopedic surgery to secure and stabilize a very severe fracture. The plate is screwed into place over the fracture, and the broken bone segments are thus held together. A portion of the applied loads to the bone is supported by the plate during the healing process. Several screws 16 are used to secure the plate. Different styles and lengths of these plates are used, depending upon the type and location of the fracture. The illustrated bone plate 15 represents an example of one style which may be employed.

Figure 4:
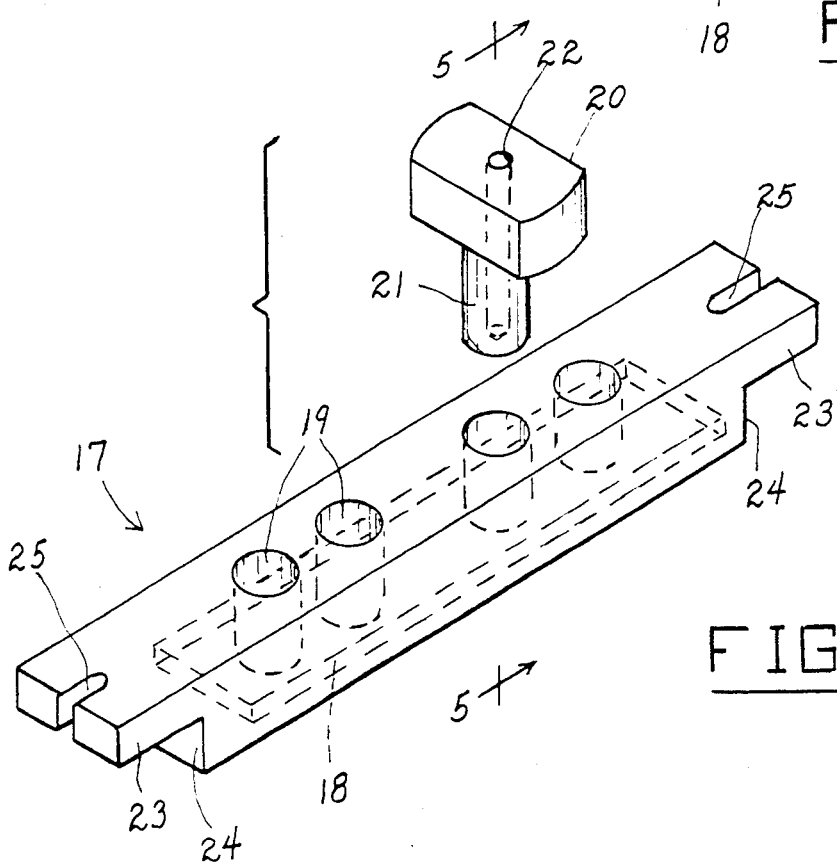
FIG. 4 is a perspective view of a drill guide block and guide bushing employed in a guide and clamp device according to the present invention.

If a bone plate is to be used, pilot holes for screws must be drilled into the bone. The pilot holes must be located so as to be in accurate registry with the screw holes provided in the bone plate. In accordance with the present invention, a guide block 17, preferably of Delrin, an acetyl resin plastic material manufactured by Dupont De Nemours E. I. & Company, Wilmington, Del., (FIG. 4) is employed for properly positioning the pilot holes drilled into the bone segments. As shown in FIG. 4, the guide block comprises an elongated member formed with a longitudinal bottom recess 18 dimensioned to closely receive the selected bone plate 15. The guide block 17 is formed with respective longitudinally spaced vertical bores 19 spaced so as to be aligned with the screw holes in the associated bone plate 15 intended to be received in said recess 18. Respective headed drill guide bushings 20 with stems 21 are provided, said stems being slidably engageable in the bores 19, each bushing 20 having an axial bore 22 employed as a drill bit guide for accurately holding the drill bit axially in its associated bore 22 when the guide block 17 is secured in working position, as will be presently described.

Guide block 17 is integrally formed with respective reduced end flanges 23, 23 forming bottom corner right-angled recesses 24, 24, and with axial longitudinal end slots 25, 25. Respective opposite end clamping assemblies 26, 26 (FIG. 6) are provided, each clamping assembly 26 having a rectangular base block 27 adjustably receivable in the right-angled recess 24 defined beneath each end flange 23. Headed clamping screws 28, 28 engage through the slots 25, 25 and are threadedly engaged in the base blocks 27, 27 for clamping the base blocks 27, 27 at an adjusted spacing therebetween on opposite sides of the fracture 14. This adjustment is provided by respective longitudinal connecting rods 29, 29 (FIG. 7) having oppositely threaded end portions 30, 31, threadely engaged in the respective base blocks 27, 27 and located symmetrically on opposite sides of the guide block 17. The connecting rods 29 have reduced hexagonal intermediate portions 32 engageable by a conventional open end wrench for rotating the connecting rods.

Figure 6:
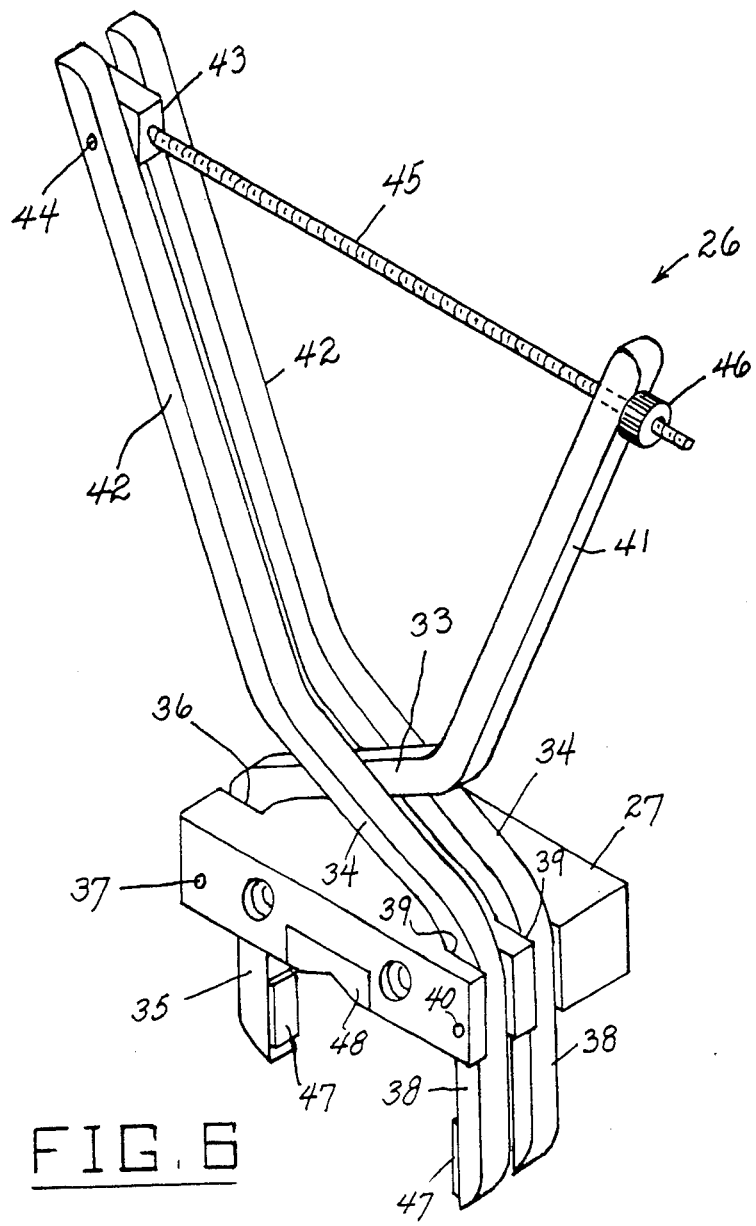
FIG. 6 is a perspective view of one of the scissor clamp assemblies employed in a guide and clamp device according to the present invention.
Figure 7:
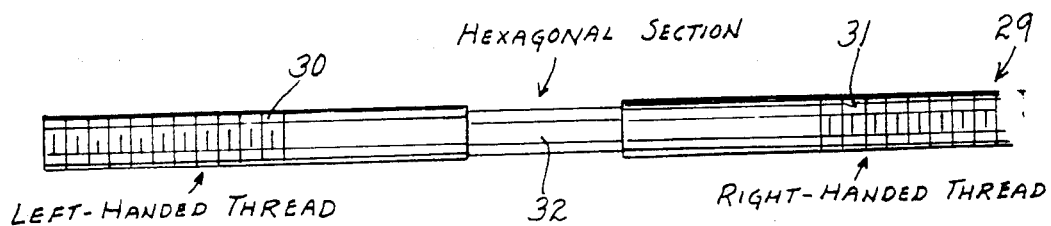
FIG. 7 is an elevational view of one of the distance-adjusting tie rods employed in a drill guide and clamp device according to the present invention.

Referring to FIG. 6, each clamping assembly 26 is of scissor-like construction, and comprises an intermediate arm 33 extending movably between a pair of parallel cooperating arms 34, 34. Intermediate arm 33 has a depending lower jaw 35 extending through an open-ended slot 36 vertically formed at one end porion of the associated base block 27 and pivotally connected therein by a transverse pin 37. The parallel arms 34, 34 have respective depending lower jaws 38, 38 extending through side-by-side vertical end slots 39, 39 in block 27 and pivotally connected therein by a transverse pin 40.

Arm 33 has an outwardly inclined top handle portion 41, and arms 34, 34 have parallel outwardly inclined top handle portions 42, 42. Pivotally connected at 44 between the top ends of handle portions 42, 42 is a bearing block 43 to which is rigidly connected a threaded tension rod 45 which extends through the top end portion of handle 41 and is provided with an outer tension-adjusting nut 46. Adjusting the nut 46 on screw rod 45 to move the handle members 41 and 42,42 towards each other tends to rotate jaw elements 35 and 38,38 towards each other, thereby providing adjustable clamping action on a bone segment received therebetween.

The cooperating scissor arms 38 and 34,34 are pivoted in parallel transverse planes relative to the associated base block 27, so that the clamping forces are perpendicularly opposed and balanced, exerting balanced clamping forces on the bone segment engaged between the depending jaws 35 and 38,38. Delrin pads 47 are secured on the jaw-gripping faces and are deformable to distribute the stresses around the bone, avoiding point contact. The flat jaw faces are preferably designed to angle inwardly slightly. This design allows different-sized bones to be held securely and forces the bone upwardly, tangent to the base block 27 of the clamp assembly. A Delrin block 48 with a V-notch is mounted longitudinally in the bottom midportion of each base block 27 to assist in holding the bone securely.

Under clamping conditions the three cooperating jaw elements 38, 35, 38 hold the bone segment steady, with a tripod grip. The Delrin contact elements 47 and 48 also protect the bone by avoiding bone-to-metal contact. The Delrin material is bone-compatible.

The procedure for the internal fixation of fractures, using the device 11 of the present invention, begins, as with all methods of internal fixation of fractures, with the making of an incision over the area of the fracture and cleaning the tissue from the damaged area. The device 11 is then engaged over the bone, with the bone plate 15 positioned in and held in the recess 18. The bone is then clamped on one side of the fracture. After aligning the bone, the other clamp 26 is tightened to stabilize the break. If necessary, the rods 29 connecting the clamps 26 are adjusted for better alignment. Pilot holes for the screws 16 are then drilled through the bores 22 of the bushings 20. The bushings 20 are then removed and the area is irrigated to flush out the drilling debris. The screws 16 are then inserted into the bone via the bores 19, and are tightened, thereby fastening the bone plate 15 to the bone segments. Following the successful placement of the screws, the guide/clamp system 11 is removed from over the bone and bone plate. If necessary, the screws 16 are retightened to provide proper compression. The bone plate 15 is now securely held to the bone. Finally, the surgeon closes the wound in the normal manner.

The various parts of the device 11 are preferably made of stainless steel or Delrin. Both stainless steel and Delrin retain their mechanical properties after undergoing normal sterilization processing, such as autoclaving.

Since there are many different sizes and styles of bone plates 15, a drill guide block 17 must be made for each size of bone plate. A guide block 17 cast from Delrin could be packaged with each bone plate 15 to prevent mismatching and to reduce the necessary inventory.

Some surgeons prefer to use compression techniques to secure the fracture, on the theory that compressing the broken bones together increases to rate of healing. To utilize the system of the present invention for compression, the connecting rods 29 must be modified to allow for greater transverse motion, such as by employing relatively loose threaded fits of the tie rods 29 with the base block members 27, 27. Also, the clamp assemblies 26 should be strengthened.

While a specific embodiment of an improved drill guide device for bone plate fixation has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A drill guide apparatus for bone plate fixation comprising an elongated drill guide block formed with a bottom recess for receiving and positioning a bone plate of the type having a plurality of spaced screw openings, the guide block having spaced openings arranged to axially align with the bone plate screw openings, respective bone clamping means adjacent the opposite end portions of said guide block, means adjustably securing said bone clamping means to the opposite ends of the guide block, and removable bushing means in at least one of the guide block openings, said bushing means being provided with an axial drill guide bore arranged to align with a subjacent bone plate screw opening.

2. The drill guide apparatus of claim 1, and wherein said guide block is formed with longitudinal end slots and wherein said means adjustably securing said bone clamping means to the guide block includes fastening means extending through said end slots.

3. The drill guide apparatus of claim 1, and means adjustably spacing said respective bone clamping means from each other.

4. The drill guide apparatus of claim 3, and wherein said spacing means comprises at least one tie bar element having oppositely threaded ends threadedly engaging said respective bone clamping means.

5. The drill guide apparatus of claim 1, and wherein the bone clamping means includes at least one scissor assembly having a base member, opposing bone-engaging depending jaws pivoted to opposite sides of said base member, respective transversely oppositely offset upstanding handle means connected to said jaws, and tensioning means connecting the handle means.

6. The drill guide apparatus of claim 5, and wherein said tensioning means comprises a tie rod pivoted to one of the upstanding handle means and extending through the opposite handle means, and a clamping nut threadedly engaged on said tie rod outwardly adjacent said opposite handle means.

7. The drill guide apparatus of claim 1, and wherein the bone clamping means comprises respective scissor assemblies adjustably secured to the opposite ends of the guide block, each scissor assembly having a base member, opposing bone-engaging depending jaws pivoted to opposite sides of the base member, respective transversely oppositely offset upstanding handle means connected to the jaws, and tensioning means connecting the upstanding handle means, and means adjustably spacing the base members relative to each other in the direction of said elongated guide block.

8. The drill guide apparatus of claim 7, and wherein said means adjustably spacing the base members comprises longitudinal tie rod means on opposite sides of the elongated guide block, said rod means having oppositely threaded end portions threadedly engaged with the base members.

9. The drill guide apparatus of claim 7, and wherein said tie rod means is provided with a non-circular portion drivingly engageable by a wrench.

10. The drill guide apparatus of claim 7, and wherein said tensioning means comprises a tie rod member pivotally connected to one of the upstanding handle means and extending through the opposite upstanding handle means, and a clamping nut threaded on the outer portion of the tie rod member.

11. The drill guide apparatus of claim 7, and wherein each scissor assembly has two spaced parallel depending jaws pivoted to one side of the base member and one opposing depending jaw pivoted to the opposite side of the base member in a transverse vertical plane between the two spaced parallel depending jaws, the jaws being provided with respective transversely offset upstanding handle portions coplanar with the depending jaws, defining said upstanding handle means.

12. The drill guide apparatus of claim 11, wherein said tensioning means is pivotally connected between the pair of upstanding handle portions at one side of the scissor assembly and extends through the opposite handle portion of said scissor assembly, and wherein said tensioning means is provided outwardly with an adjustable clamping nut threaded thereon.

13. The drill guide apparatus of claim 1, and wherein the bone clamping means includes at least one scissor assembly having a base member, opposing depending jaws pivoted to opposite sides of said base member, respective transversely oppositely offset upstanding handle means connected to the jaws, tensioning means connecting the upstanding handle means, and Delrin bone-contacting pads secured on the inner faces of the jaws.

14. The drill guide apparatus of claim 13, and Delrin bone-contacting longitudinal pad means mounted substantially centrally in the downwardly-facing portion of the base member.

15. The drill guide apparatus of claim 1, and wherein said bone clamping means is provided with Delrin pad means at its bone-contacting surfaces.

16. A drill guide apparatus comprising an elongated guide block formed to receive and position a bone plate in its bottom, the guide block having openings located to axially align with the bone plate screw openings, respective bone clamps secured to the opposite ends of the guide block, and removable bushing means in at least one of the guide block openings, the bushing means being formed with a guide bore arranged to align with a subjacent bone plate screw opening.

* * * * *